United States Patent
Keeble et al.

(10) Patent No.: US 9,439,758 B2
(45) Date of Patent: Sep. 13, 2016

(54) BLOOD VESSEL PROSTHESIS AND DELIVERY APPARATUS

(75) Inventors: Thomas Keeble, London (GB); Martin Rothman, London (GB)

(73) Assignee: Barts and the London NHS Trust, London (GB)

( * ) Notice: Subject to any disclaimer, the term of this patent is extended or adjusted under 35 U.S.C. 154(b) by 456 days.

(21) Appl. No.: 12/918,052

(22) PCT Filed: Feb. 23, 2009

(86) PCT No.: PCT/GB2009/000485
§ 371 (c)(1),
(2), (4) Date: Jan. 28, 2011

(87) PCT Pub. No.: WO2009/104000
PCT Pub. Date: Aug. 27, 2009

(65) Prior Publication Data
US 2011/0166644 A1    Jul. 7, 2011

(30) Foreign Application Priority Data
Feb. 22, 2008 (GB) .................................. 0803302.9

(51) Int. Cl.
*A61F 2/07* (2013.01)
*A61F 2/24* (2006.01)
(Continued)

(52) U.S. Cl.
CPC ............... *A61F 2/2418* (2013.01); *A61F 2/07* (2013.01); *A61F 2/24* (2013.01); *A61F 2/2409* (2013.01); *A61F 2/2412* (2013.01); *A61F 2/2427* (2013.01); *A61F 2/2442* (2013.01); *A61F 2/82* (2013.01); *A61F 2/856* (2013.01); *A61F 2/89* (2013.01); *A61F 2/915* (2013.01); *A61F 2/95* (2013.01); *A61F 2/954* (2013.01); *A61F 2002/061* (2013.01); *A61F 2002/075* (2013.01);
(Continued)

(58) Field of Classification Search
USPC ................................................ 623/1.13, 1.35
See application file for complete search history.

(56) References Cited

U.S. PATENT DOCUMENTS

| | | |
|---|---|---|
| 4,733,665 A | 3/1988 | Palmaz |
| 4,739,762 A | 4/1988 | Palmaz |

(Continued)

FOREIGN PATENT DOCUMENTS

| | | |
|---|---|---|
| CA | 2580952 A1 | 9/2005 |
| EP | 0646365 | 4/1995 |

(Continued)

OTHER PUBLICATIONS (Journal article) K. inoue et al., Aortic Arch Reconstruction by Transluminally Placed Enovascular Branched Stent Graft, Circulation. 1999; 100.

*Primary Examiner* — Yashita Sharma
*Assistant Examiner* — Rebecca Preston
(74) *Attorney, Agent, or Firm* — Seed IP Law Group PLLC

(57) ABSTRACT

A prosthesis for locating at a branch region of a blood vessel. The prosthesis comprises a main conduit (10) having a tubular portion (11) with first and second ends (12,13), and at least one projecting portion (14,15,16) projecting from the first end of the tubular portion. One or more branch conduits (17,18) are connected to, and extend from the projecting portions or the tubular portion at a position adjacent the projecting portions. Portions of the prosthesis to which the branch conduits are attached may be more flexible and/or elastic than other portions of the prosthesis.

9 Claims, 14 Drawing Sheets

(51) Int. Cl.
*A61F 2/82* (2013.01)
*A61F 2/856* (2013.01)
*A61F 2/915* (2013.01)
*A61F 2/95* (2013.01)
*A61F 2/954* (2013.01)
*A61F 2/06* (2013.01)
*A61F 2/958* (2013.01)
*A61F 2/89* (2013.01)

(52) U.S. Cl.
CPC .... *A61F2002/821* (2013.01); *A61F 2002/825* (2013.01); *A61F 2002/9583* (2013.01); *A61F 2230/0013* (2013.01); *A61F 2230/0054* (2013.01); *A61F 2230/0069* (2013.01); *A61F 2250/0069* (2013.01)

(56) References Cited

U.S. PATENT DOCUMENTS

| | | |
|---|---|---|
| 4,856,516 A | 8/1989 | Hillstead |
| 4,913,141 A | 4/1990 | Hillstead |
| 4,950,227 A | 8/1990 | Savin et al. |
| 5,019,090 A | 5/1991 | Pinchuk |
| 5,037,141 A | 8/1991 | Jardine |
| 5,178,634 A | 1/1993 | Ramos Martinez |
| 5,342,300 A | 8/1994 | Stefanis et al. |
| 5,360,401 A | 11/1994 | Turnland |
| 5,387,193 A | 2/1995 | Miraki |
| 5,489,297 A * | 2/1996 | Duran .......... 623/2.13 |
| 5,609,627 A | 3/1997 | Golcoechea et al. |
| 5,653,743 A | 8/1997 | Martin |
| 5,709,713 A | 1/1998 | Evans et al. |
| 5,749,825 A | 5/1998 | Fischell |
| 5,755,770 A | 5/1998 | Ravenscroft |
| 5,782,904 A | 7/1998 | White et al. |
| 5,824,040 A | 10/1998 | Cox et al. |
| 5,824,064 A | 10/1998 | Taheri |
| 5,843,158 A | 12/1998 | Lenker et al. |
| 5,904,713 A | 5/1999 | Leschinsky |
| 5,925,061 A | 7/1999 | Ogi et al. |
| 5,984,955 A | 11/1999 | Wisselink |
| 6,099,548 A | 8/2000 | Taheri |
| 6,099,559 A | 8/2000 | Nolting |
| 6,187,033 B1 | 2/2001 | Schmitt et al. |
| 6,334,867 B1 | 1/2002 | Anson |
| 6,344,056 B1 | 2/2002 | Dehdashtian |
| 6,482,228 B1 | 11/2002 | Norred |
| 6,544,285 B1 * | 4/2003 | Thubrikar et al. .......... 623/2.12 |
| 6,641,606 B2 | 11/2003 | Ouriel et al. |
| 6,730,118 B2 | 5/2004 | Spenser et al. |
| 6,770,090 B2 | 8/2004 | Gantt et al. |
| 6,773,457 B2 | 8/2004 | Ivancev et al. |
| 6,790,230 B2 | 9/2004 | Beyersdorf et al. |
| 6,827,726 B2 | 12/2004 | Parodi |
| 6,860,900 B2 | 3/2005 | Clerc et al. |
| 6,866,650 B2 | 3/2005 | Stevens |
| 6,949,121 B1 | 9/2005 | Laguna |
| 6,989,024 B2 | 1/2006 | Hebert et al. |
| 6,994,700 B2 | 2/2006 | Elkins et al. |
| 7,018,404 B2 * | 3/2006 | Holmberg et al. .......... 623/1.26 |
| 7,018,406 B2 | 3/2006 | Seguin et al. |
| 7,037,331 B2 | 5/2006 | Mitelberg et al. |
| 7,041,079 B2 | 5/2006 | Yozu et al. |
| 7,044,966 B2 | 5/2006 | Svanidze et al. |
| 7,201,772 B2 | 4/2007 | Schwammenthal et al. |
| 2002/0082684 A1 | 6/2002 | Mishaly |
| 2002/0156518 A1 * | 10/2002 | Tehrani .......... 623/1.11 |
| 2003/0004567 A1 | 1/2003 | Boyle et al. |
| 2003/0036791 A1 | 2/2003 | Philipp et al. |
| 2003/0153968 A1 | 8/2003 | Geis et al. |
| 2004/0073288 A1 | 4/2004 | Kerr |
| 2004/0098091 A1 | 5/2004 | Erbel et al. |
| 2004/0116997 A1 | 6/2004 | Taylor et al. |
| 2004/0133266 A1 | 7/2004 | Clerc et al. |
| 2004/0204754 A1 | 10/2004 | Kaplan et al. |
| 2004/0210304 A1 | 10/2004 | Seguin et al. |
| 2005/0033406 A1 * | 2/2005 | Barnhart et al. .......... 623/1.13 |
| 2005/0131517 A1 | 6/2005 | Hartley et al. |
| 2005/0154444 A1 | 7/2005 | Quadri |
| 2005/0222674 A1 | 10/2005 | Paine |
| 2005/0234546 A1 * | 10/2005 | Nugent et al. .......... 623/2.11 |
| 2005/0240257 A1 | 10/2005 | Ishimaru |
| 2006/0004436 A1 | 1/2006 | Amarant et al. |
| 2006/0052865 A1 | 3/2006 | Banas |
| 2006/0069323 A1 | 3/2006 | Elkins et al. |
| 2006/0095118 A1 | 5/2006 | Hartley et al. |
| 2006/0155363 A1 | 7/2006 | Laduca et al. |
| 2006/0155366 A1 | 7/2006 | Laduca et al. |
| 2006/0224236 A1 | 10/2006 | Thistle |
| 2006/0229719 A1 * | 10/2006 | Marquez et al. .......... 623/2.41 |
| 2006/0276813 A1 * | 12/2006 | Greenberg .......... 606/158 |
| 2006/0287717 A1 | 12/2006 | Rowe et al. |
| 2007/0032852 A1 * | 2/2007 | Machek et al. .......... 623/1.13 |
| 2007/0055350 A1 | 3/2007 | Erickson et al. |
| 2007/0083215 A1 | 4/2007 | Hamer et al. |
| 2007/0100440 A1 | 5/2007 | Figulla et al. |
| 2007/0150051 A1 | 6/2007 | Arnault de la Menardiere et al. |
| 2007/0233220 A1 | 10/2007 | Greenan |
| 2008/0275548 A1 * | 11/2008 | Svensson .......... 623/2.1 |
| 2009/0118826 A1 * | 5/2009 | Khaghani .......... 623/2.12 |
| 2010/0057181 A1 * | 3/2010 | Rothman .......... 623/1.11 |
| 2011/0288627 A1 | 11/2011 | Hartley et al. |

FOREIGN PATENT DOCUMENTS

| | | |
|---|---|---|
| EP | 0832618 | 4/1998 |
| EP | 1029518 | 8/2000 |
| EP | 1117348 | 7/2001 |
| EP | 1161268 | 12/2001 |
| EP | 1330993 | 7/2003 |
| EP | 1656906 | 5/2006 |
| EP | 1759666 | 3/2007 |
| GB | 2398245 | 8/2004 |
| WO | 91/17720 | 5/1991 |
| WO | 95/03754 A | 2/1995 |
| WO | 96/24308 | 8/1996 |
| WO | 97/17101 | 5/1997 |
| WO | 98/19629 | 5/1998 |
| WO | 99/33412 A | 7/1999 |
| WO | 99/36002 | 7/1999 |
| WO | 00/12168 | 3/2000 |
| WO | 00/42948 | 7/2000 |
| WO | 00/44309 | 8/2000 |
| WO | 01/52776 A | 7/2001 |
| WO | 02/056799 | 7/2002 |
| WO | 02056799 | 7/2002 |
| WO | 02/076346 | 10/2002 |
| WO | 03/065933 | 8/2003 |
| WO | 03/068302 | 8/2003 |
| WO | 03/082153 | 10/2003 |
| WO | 2005/000168 A | 1/2005 |
| WO | 2005/037141 | 4/2005 |
| WO | 2005/122957 | 12/2005 |
| WO | 2006/047184 A | 5/2006 |
| WO | 2007/026991 | 3/2007 |
| WO | 2007/028112 | 3/2007 |
| WO | 2007/051179 | 5/2007 |
| WO | 2007/058857 | 5/2007 |
| WO | 2007/071436 | 6/2007 |
| WO | 2007/079081 | 7/2007 |
| WO | 2007/081820 | 7/2007 |
| WO | 2007/146021 | 12/2007 |

* cited by examiner

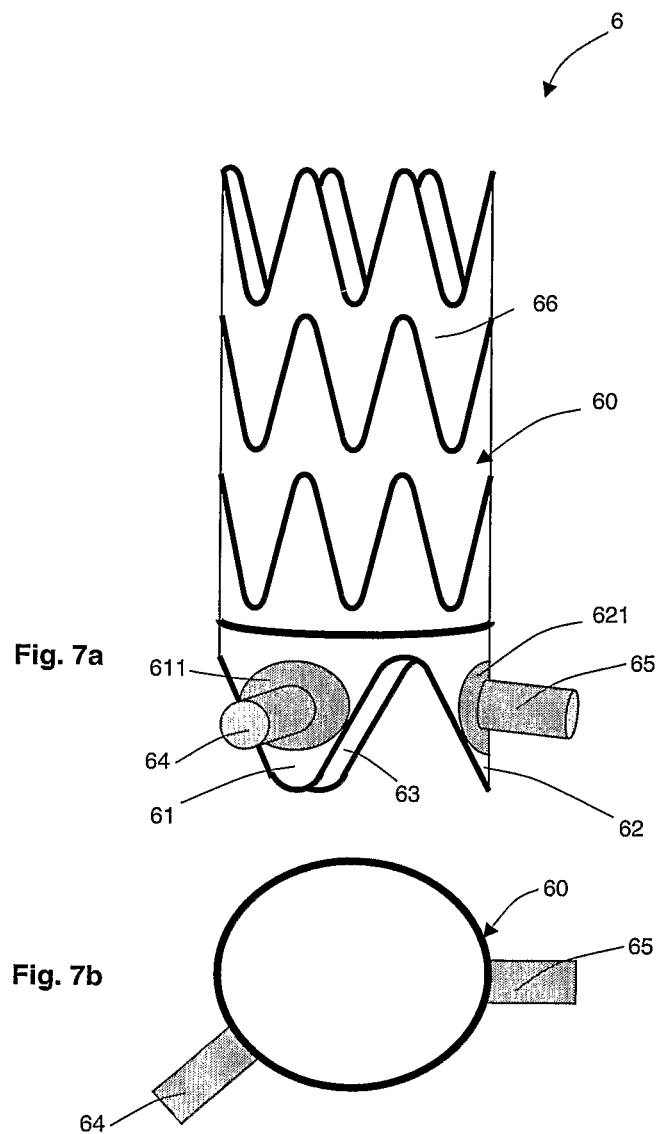

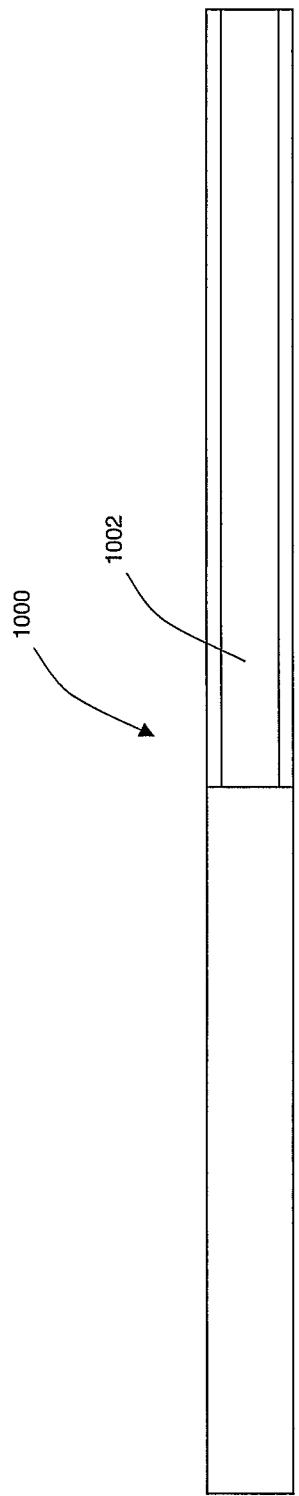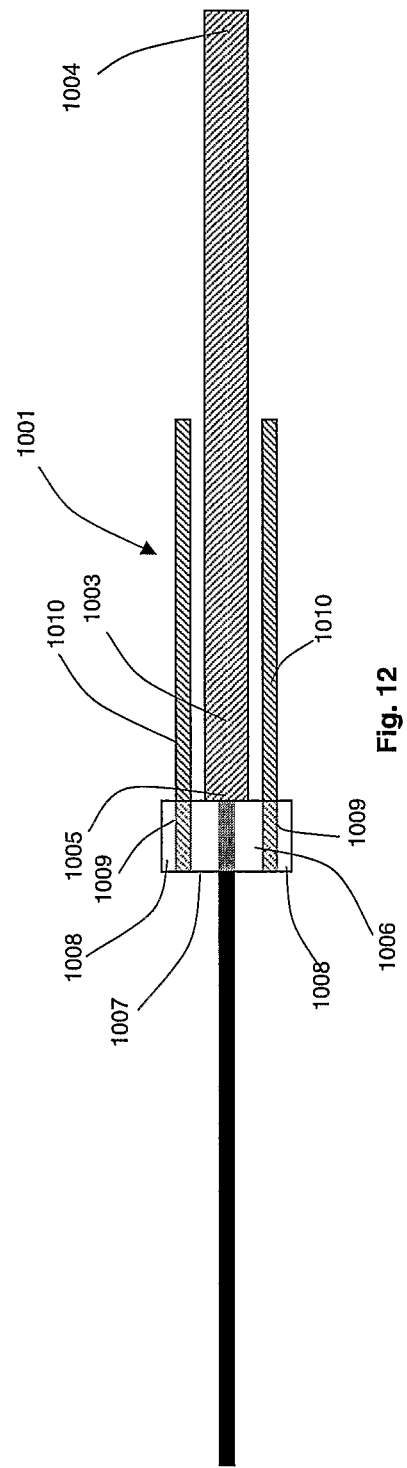

BLOOD VESSEL PROSTHESIS AND DELIVERY APPARATUS

CROSS-REFERENCE TO RELATED APPLICATIONS

This application claims priority to International Application No. PCT/GB2009/000485, filed on Feb. 23, 2009, which claims priority to Great Britain Patent Application No. 0803302.9, filed Feb. 22, 2008, each of which is incorporated by reference in its entirety.

The invention relates to a prosthesis for a blood vessel, and a delivery apparatus for delivering the prosthesis to the blood vessel, particularly, but not necessarily exclusively, for use in the treatment of aneurysms or dissections of the blood vessel.

Aneurysms are permanent distensions of the wall of a blood vessel, e.g. an artery, which disrupt the haemodynamics of the blood vessel. The aneurysm may halt the flow of blood at certain regions of the blood vessel, increasing the risk of clot formation, which may in turn cause cerebral embolism. Furthermore, a reduction in the structural wall integrity of the blood vessel may occur, which can cause a reduction in the effectiveness of the blood vessel and put a higher strain on the heart muscle, increasing the risk of heart failure or vessel rupture.

Dissections are tears in the blood vessel's intima or delaminations of the collagen/elastin wall architecture of the blood vessel. Dissections can result in a false lumen, i.e. inner cavity, within the blood vessel. The false lumen may provide areas in which blood can pool, increasing the risk of clot formation and subsequent cerebral embolism. Severe dissection may even result in a breach of the blood vessel integrity and possible bleeding from the blood vessel e.g. into the thoracic cavity, which may cause death in a short period of time.

A branch region, particularly prone to aneurysms and dissections, is the region of the ascending aorta where the aortic root meets the right and left coronary arteries, which feed the heart muscle with oxygenated blood. The aortic root includes the aortic valve, at the interface between the left ventricle and the aorta, which permits oxygenated blood to enter the aorta. The ostia of the coronary arteries are located very close to the aortic valve.

Traditional treatment for dissections and aneurysms include surgical resection, removing the offending tissue (depending on the extent of the damage to the blood vessel), or the insertion of a tubular prosthesis or stent grant within the lumen of the blood vessel to remove the mechanical loading on the damaged blood vessel wall and to provide a haemodynamically compatible conduit for the transport of blood. Prostheses are traditionally made from Dacron® or high density Polytetrafluoroethylene (PTFE).

Prostheses and stent grafts have been designed for positioning at bifurcation regions of blood vessels, i.e. regions in which the blood vessel branches. For example, WO00042948, WO03082153, WO05122957 and U.S. Pat. No. 5,984,955 disclose bifurcated prostheses/stent grafts for positioning primarily at the iliac bifurcation of the aorta. The prostheses comprise a main conduit, a first branch conduit and a second branch conduit. The main conduit is designed to locate within the aorta and the first and second branch conduits are designed to locate within respective iliac arteries.

Journal article: K. Inoue et al., "Aortic Arch Reconstruction by Transluminally Placed Endovascular Branched Stent Graft", *Circulation*. 1999; 100 describes a stent graft which includes conduits for aortic branches and a method of introduction.

Prostheses and stent grafts have been designed for locating at the aortic root, which prostheses comprise artificial valves, for replacing or providing back-up for damaged aortic valves. Examples of such prostheses can be found in U.S. Pat. Nos. 6,482,228, 6,790,230 and US2006155363 and EP0592410.

According to a first aspect of the present invention, there is provided a prosthesis for locating at a branch region of a blood vessel, the prosthesis comprising:
  a main conduit having a tubular portion with first and second ends, and a first projecting portion, the first projecting portion projecting from the first end of the tubular portion, and
  a first branch conduit, wherein the first branch conduit is connected to, and extends from:
    (a) the first projecting portion, or
    (b) the tubular portion at a position adjacent the first projecting portion.

By positioning the prosthesis within the branch region of the blood vessel it can relieve the mechanical loading on the blood vessel itself.

According to a second aspect of the present invention, there is provided a method of delivering a prosthesis to a branch region of a blood vessel, the branch region having a main blood vessel and one or more branch blood vessels, the method comprising the steps of:
  providing a prosthesis comprising:
    a main conduit having a tubular portion with first and second ends, and a first projecting portion, the first projecting portion projecting from the first end of the tubular portion, and
    a first branch conduit, wherein the first branch conduit is connected to, and extends from:
      (a) the first projecting portion; or
      (b) the tubular portion at a position adjacent the first projecting portion, and
  delivering the prosthesis to the branch region of the blood vessel such that the main conduit locates in the main blood vessel and the first branch conduit locates in one of the branch blood vessels.

Preferably, the prosthesis of the first and/or second aspects of the invention comprises a second projecting portion which projects from the first end of the main conduit, and a second branch conduit connected to, and extending from: (a) the second projecting portion, or (b) the tubular portion at a position adjacent the second projecting portion. A gap is provided between the first and second projecting portions. The second branch conduit is for locating in another of the branch blood vessels.

When the branch conduits are connected to the tubular portion, adjacent the projecting portions, preferably the branch conduits are connected at a position no more than 1 cm, more preferably no more than 0.5 cm, and most preferably no more than 0.2 cm from the first end of the tubular portion.

The projecting portions may be connected to both the tubular portion and the projecting portions.

Preferably, the prosthesis is for deploying at the branch region of the aortic root, where the aorta meets the right and left coronary arteries, the main conduit, first branch conduit and second branch conduit being for locating in the aorta, the right coronary artery and the left coronary artery respectively.

By arranging the first and second branch portions to extend from the first and second projecting portions, or a position on the main conduit adjacent the projecting portions, interference between the prosthesis and the aortic valve may be prevented. In more detail, with reference to FIG. 1, which depicts very generally the arrangement of an aortic root 10, the aortic valve 100 is located at the bottom of the ascending aorta adjacent the left and right coronary arteries 101, 102. The valve 100 comprises three valve leaflets 103. Side edges 104 of each leaflet 103 are releasably engaged to side edges 104 of adjacent valve leaflets 103. The leaflets 103 are generally half-mooned shape, each forming a bowl-shaped cavity. The leaflets 103 rise up towards their side edges 104 so as to form three radially extending ridges 105 where the adjacent side edges meet. The ridges 105 rise up from a central region 106 of the valve 100, to commissural points 107 (i.e. points at which the side edges join) positioned at the periphery of the valve 100. The arrangement of the aortic valve 100 is such that the ridges 105 may extend to commissural points 107 higher than the coronary ostia 108 provided in the walls of the aorta in a central region between the ridges 105.

It is preferable that, for use with a patient in which the ridges of the patient's aortic valve extend higher than the coronary ostia, the branch conduits are connected to the projecting portions. In these circumstances, if the first and second branch portions of the prosthesis were instead arranged to connect to and extend from the tubular portion of the main conduit, the tubular portion may be forced to extend lower than the ridges of the aortic valve, causing interference between the main conduit and the aortic valve. This could cause damage to the aortic valve and/or cause it to malfunction. However, in this aspect of the present invention, the prosthesis is provided with projecting portions, which portions may project between the ridges of the aortic valve, into the bowl-shaped cavities of the leaflets, thus negotiating the ridges without interference. When there is more than one projecting portion, a gap provided between adjacent projecting portions accommodates the ridges.

When, however, the prosthesis is for use with a patient in which the ridges of the patient's aortic valve do not extend higher than the coronary ostia, the branch conduits may be connected to either the tubular portion or the projecting portions. If one or both branch conduits is connected to the tubular portion, it is advantageous to have projecting portions adjacent the connection points because it will provide additional structure to the main conduit on the projecting portion side of the branch conduits, the structure being arranged such that it may not necessarily interfere with the aortic valve, as discussed above. By providing additional structure, the branch conduits may be positioned in the coronary ostia more securely.

Very generally, the projecting portions may be considered as extensions of the tubular portion that do not extend around the entire circumference of the tubular portion, and can therefore have gaps between them into which the ridges of the aortic valve may fit.

It is considered, nevertheless, that the prosthesis of the present invention may be used for branch regions of blood vessels other than the branch region at the aortic root, where a different obstacle to the aortic valve must be navigated to allow the branch conduits to be placed in branch blood vessels.

The projecting portions may each comprise wall material that is identical or different to the wall material of the tubular portion of the main conduit. The walls of each projecting portion may connect to rim or annular region at the first end of the tubular portion. Preferably, each projecting portion connects to a region of the tubular wall portion which extends around less than half, more preferably less than a third, of the circumference of the tubular wall portion. Preferably, the projecting portions have rounded edges, in which case the projecting portions may be considered as lobes. By having rounded edges, damage to blood vessels upon contact with the projecting portions may be minimised, and the projecting portions may have a configuration more appropriate for fitting within the bowl-shaped cavities provided by the valve leaflets, between the ridges of the valve.

The projecting portions may project from the first end of the tubular wall portion of the main conduit in the elongation direction of the tubular portion, the elongation direction being the direction of extension of the tubular portion between its first and second ends. Alternatively, the projecting portions may project in a direction angled from the elongation direction of the tubular portion. Preferably, the projecting portions project in a direction which is less than 90 degrees, more preferably less than 45 degrees from the elongation direction of the tubular portion.

Preferably, the prosthesis comprises a scaffold that supports wall material of the tubular portion and may also support wall material of the projecting portions. The scaffold may include one or more wire rings. The wire rings may follow a zigzagging path. The wire rings may be z-stents or stents of another form.

There may be two, three or more wire rings (e.g. stents) or other scaffold members spaced from one another along the prosthesis.

One or more additional scaffold members, for example tie bars, may be used to link adjacent wire rings. These linking scaffold members may extend generally longitudinally along the prosthesis between the wire rings. There may be one, two, three or more linking members connection each adjacent pair of wire rings in the scaffold.

In some embodiments, the linking scaffold members are arranged asymmetrically around the perimeter of the prosthesis. For instance, the linking members may be arranged towards one side of the prosthesis so that they substantially prevent the wire rings from moving apart from one another on that side, whilst allowing the wire rings to move further from one another on the opposite side, allowing the prosthesis to curve towards said one side. This may be desirable, for example, to enable the prosthesis to adopt the curvature of the aorta or other vessel in which it is to be deployed.

Where the scaffold comprises three or more wire rings, linking members linking respective adjacent pairs of wire members are preferably not aligned with one another. The linking members connecting a first and second wire ring may, for example, be more closely spaced around the perimeter of the prosthesis than those connecting the second wire ring to a third wire ring. With appropriate selection of the relative positions of the linking members, for example to leave a smaller or bigger arc of said opposite side of a portion of the prosthesis between adjacent wire rings free of linking members the amount and direction of possible curvature of the prosthesis can be controlled.

One of the wire rings may be located adjacent the first end of the tubular portion. The zigzags of this wire ring may project from the tubular portion and serve to define the outer edges of the projecting portions.

The prosthesis may comprise a prosthetic valve, e.g. a prosthetic aortic valve. This may be employed when, for example, the actual aortic valve is damaged. The prosthetic aortic valve may have substantially the same configuration as the actual aortic valve, described above. For example it may comprise three valve leaflets, side edges of each leaflet being releasably engaged to side edges of adjacent valve leaflets. The leaflets may be substantially half-mooned shape, each forming a bowl-shaped cavity. The leaflets may rise up towards their side edges so as to form three radially extending ridges where the adjacent side edges meet. The ridges may rise up from a central region of the valve, to commissural points positioned at the periphery of the valve.

The artificial aortic valve may be provided adjacent the projecting portions of the main conduit. Preferably, in these circumstances, the commissural points are connected to the tubular portion of the main conduit between adjacent projecting portions.

Preferably, the tubular portion comprises a circumferential sealing element on its outer side, to prevent blood flowing between it, and the walls of the ascending aorta, in use. Preferably, the sealing element is provided adjacent the first end of the tubular portion. The sealing element may locate, in use, at the sinotubular junction. Nevertheless, the sealing element may be located anywhere between the first and second ends of the tubular portion.

Preferably, the prosthesis can be moved between expanded and contracted states. The prosthesis may be placed in a contracted state during delivery to the branch region, so that it is less likely to be obstructed during delivery. Then, once positioned at the branch region, it may be expanded for use. Preferably, the prosthesis is arranged such that, when the prosthesis is placed in a contracted state, the walls of the projecting portions partially or entirely envelop the branch conduits connected or adjacent thereto. Accordingly, the prosthesis may take a more compact and streamlined form, reducing the chances that the branch conduits are impeded during delivery to the branch region.

Although the projecting portions of the prosthesis may be employed to minimise contact between the prosthesis and the aortic valve, as discussed above, it is also conceived that, when the prosthesis comprises a prosthetic aortic valve, the projecting portions may be arranged such that they press against the actual aortic valve, causing it to open. The projecting portions may press one or more of the valve leaflets against the walls of the blood vessel. By maintaining the actual aortic valve in an open position, potential complications with having two valves working at the same time can be avoided. By employing projecting portions to push the aortic valve open, appropriate parts of the aortic valve to push, e.g. central regions of the valve leaflets, can be targeted. Furthermore, the amount of material of the main conduit may be minimised, allowing the prosthesis to take a more compact form in its collapsed state.

According to a third aspect of the present invention, there is provided a prosthesis for locating at the branch region of the aortic root where the aorta meets the right and left coronary arteries, the prosthesis comprising:
 a main conduit for locating in the aorta, the main conduit having first and second ends, the first end being for locating in the aortic root upstream of the second end;
 a first branch conduit connected to the main conduit at a position located between the first and second ends of the main conduit, the first branch conduit being for locating in one of the left and right coronary arteries, and
 a prosthetic aortic valve,
 wherein the distance between the connection of the first branch conduit and the main conduit, and the first end of the main conduit, is such that, when the first branch conduit is located in one of the left and right coronary arteries, the first end of the main conduit extends to a position at which it presses against the aortic valve, maintaining the aortic valve in an open position.

According to a fourth aspect of the present invention, there is provided a method of delivering a prosthesis to the branch region of the aortic root where the aorta meets the right and left coronary arteries, the method comprising the steps of:
 providing a prosthesis comprising:
  a main conduit having first and second ends;
  a first branch conduit connected to the main conduit at a position located between the first and second ends of the main conduit, and
  a prosthetic aortic valve, and
 delivering the prosthesis to the branch region and locating the main conduit in the aorta and the first branch conduit in one of the left and right coronary arteries whereupon the first end of the main conduit presses against the aortic valve, maintaining the aortic valve in an open position.

As discussed above with respect to the first and second aspect of the invention, by maintaining the aortic valve in an open position, possible complications with having two valves working at the same time can be avoided.

Preferably the prosthesis comprises a second branch conduit connected to the main conduit, for locating in the other of the left and right coronary arteries.

Preferably, the distance between the connection position of the first branch conduit with the main conduit and the first end of the main conduit is at least 1 cm, preferably between 1 cm and 2 cm.

The main conduit may be cylindrical. It may have cylindrical walls between its first and second ends. As an alternative, the main conduit may have a tubular portion and one or more projecting portions, as discussed above with respect to the first aspect of the present invention.

Preferably, in one or more of the above aspects of the present invention, the branch conduits connect to a region of the walls of the projecting portions, main conduit or tubular portion that is flexible and/or elastic. Preferably this wall region is more elastic than the rest of the main conduit, e.g. the walls of the tubular portion. By connecting to flexible and/or elastic wall regions, the branch conduits may be moved more easily relative to the prosthesis as a whole, or relative to each other. This may provide the prosthesis with greater adaptability for use at branch regions of blood vessels which have different anatomic configurations.

According to a fifth aspect of the present invention, there is provided a prosthesis for locating at a branch region of a blood vessel, the prosthesis comprising:
 a main conduit having walls extending between first and second ends of the main conduit, and
 one or more branch conduits;
 wherein the walls of the main conduit comprise a first section and a second section, the second section being more flexible and/or elastic than the first section, and
 wherein the one or more branch conduits are connected to, and extend from, the second section.

According to a sixth aspect of the present invention, there is provided a method of delivering a prosthesis to a branch region of a blood vessel, the branch region having a main blood vessel and one or more branch blood vessels, the method comprising the steps of:
 providing a prosthesis comprising:
  a main conduit having walls extending between first and second ends of the main conduit, and
  one or more branch conduits;

wherein the walls of the main conduit comprise a first section and a second section, the second section being more flexible and/or elastic than the first section, and wherein the one or more branch conduits are connected to, and extend from, the second section; and delivering the prosthesis to the branch region of the blood vessel such that the main conduit locates in the main blood vessel and the first branch conduit locates in one of the branch blood vessels.

In the fifth and sixth aspects, preferably the branch region is the branch region of the aortic root where the aorta meets the left and right coronary arteries.

The main conduit may comprise wall material with scaffolding, as described above. So that the second section is more flexible and/or elastic than the first section, it may be have no scaffolding (e.g. no z-stents), or a reduced amount of scaffolding, to support it, than the first section. Alternatively, or additionally, the properties of the wall material of the second section (e.g. the thickness, weave and/or chemical properties of the material) may be such that the second section is more flexible and/or elastic than the first section.

The first and second sections may be circumferential wall sections of the main conduit. The walls of the main conduit may comprise a third section, e.g. a third circumferential wall section, the second section also being more flexible and/or elastic than the third section.

The second circumferential wall section may be provided intermediate the first and third circumferential wall sections, the one or more branch conduits being connected to the second circumferential wall section.

By arranging the branch conduits to connect to a more flexible and/or elastic part of the main conduit, the branch conduits may be moved significantly relative to each other, or to the prosthesis as a whole. This may provide the prosthesis with greater adaptability for use at branch regions of blood vessels which have different anatomic configurations.

Preferably, the prosthesis of any one or more of the above aspects of the present invention is delivered to the branch region percutaneously. Preferably, catheter apparatus is used to deliver the prosthesis to the branch region.

The catheter apparatus may comprise a core catheter for pushing the prosthesis to the branch region, and actuators to push the branch conduits into the respective branch blood vessels. Preferably, the core catheter is connected to a push element at its distal end, for engaging the prosthesis. The push element may have a flat distal surface for engaging the prosthesis. Preferably, the actuators are moveably mounted, e.g. slidably mounted, to the push element.

According to a seventh aspect of the present invention, there is provided a catheter apparatus for delivering a prosthesis to a branch region of a blood vessel, the prosthesis comprising a main conduit and one or more branch conduits, the catheter apparatus comprising:

a core catheter having a distal end and a proximal end;

a push element provided at the distal end of the core catheter for engaging and pushing the prosthesis, and one or more actuators for pushing the one or more branch conduits of the prosthesis;

wherein the actuators are moveably mounted to the push element.

According to an eighth aspect of the present invention, there is provided a method of delivering a prosthesis to a branch region of a blood vessel, the branch region having a main blood vessel and one or more branch blood vessels, the method comprising the steps of:

providing a prosthesis comprising a main conduit and one or more branch conduits;

providing a core catheter having a distal end and a proximal end and a push element at the distal end, wherein one or more actuators are moveably mounted to the push element;

moving the core catheter so that the push element pushes the prosthesis to the branch region, and moving the one or more actuators relative to the push element so that the actuators push the one or more branch conduits into the one or more branch blood vessels.

Preferably the prosthesis is a prosthesis as described above with respect to the first, third and/or fifth aspects of the present invention.

Preferably the actuators are slidably mounted to the push element. In the above-described aspects of the invention, the push element may comprise holes or bores, through which the actuators can extend, in order to slidably mount the actuators to the push element. The push element may have lateral regions that extend in a direction substantially perpendicular to elongation direction of the core catheter, the holes being provided in the lateral regions of the push element.

Preferably, the actuators each comprise a balloon catheter. The balloon catheter may be provided within an actuator sleeve.

Preferably, the catheter apparatus comprises a reinforced liner sleeve, the reinforced liner sleeve being for locating over the core, push element and/or actuators, whilst the catheter apparatus is moved toward the branch region. The liner sleeve may be reinforced with braided material, or spirally oriented material, for example. The liner sleeve may permit the catheter apparatus to take a compact and streamlined profile, and may prevent parts of the catheter from kinking as it negotiates tight corners, e.g. the bend of the ascending aorta.

Examples embodying the present invention are now described with reference to the accompanying drawings, in which:

FIGS. 7a and 7b show a side view and an end view respectively of a prosthesis according to a sixth embodiment of the present invention;

Figure 9:
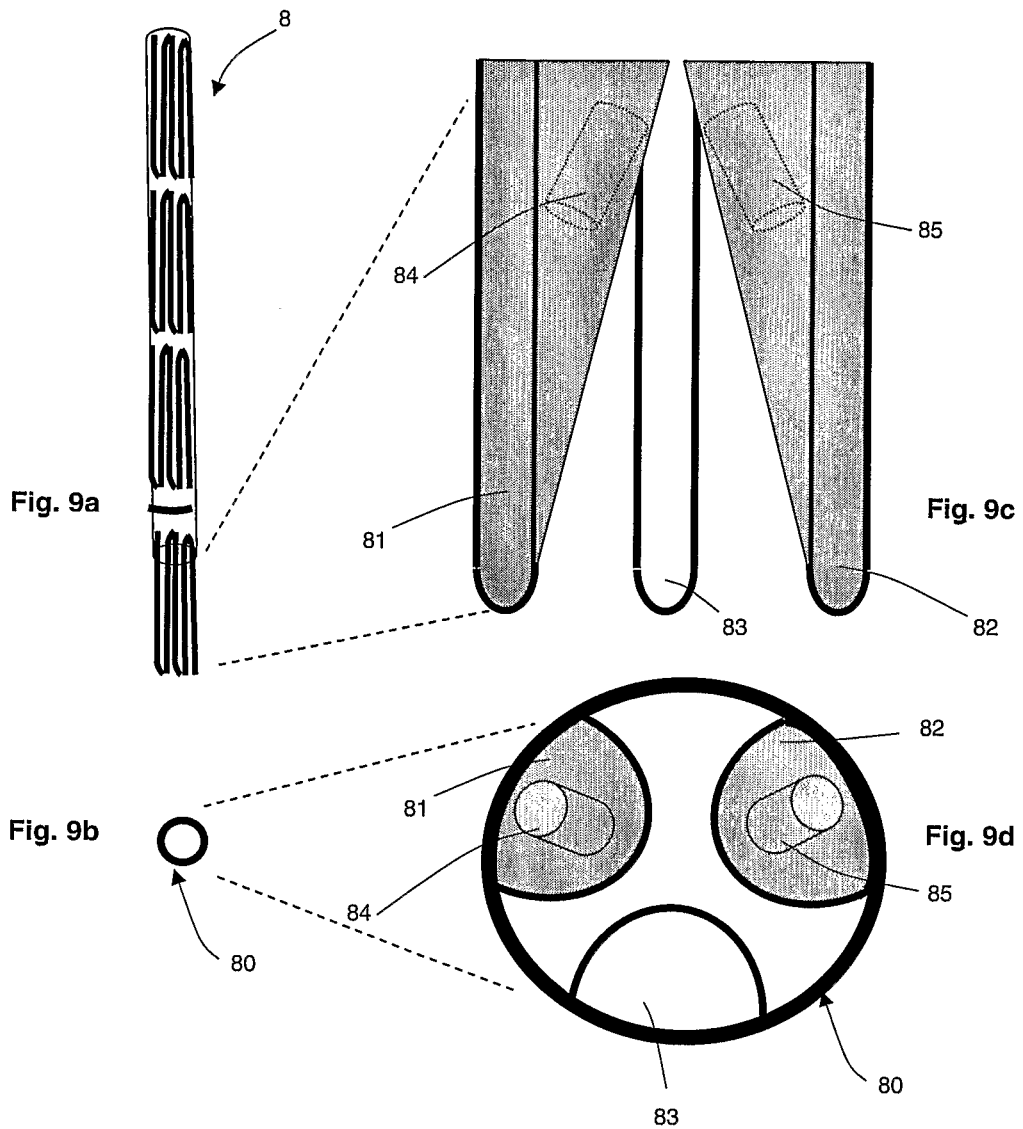
Figure 10:
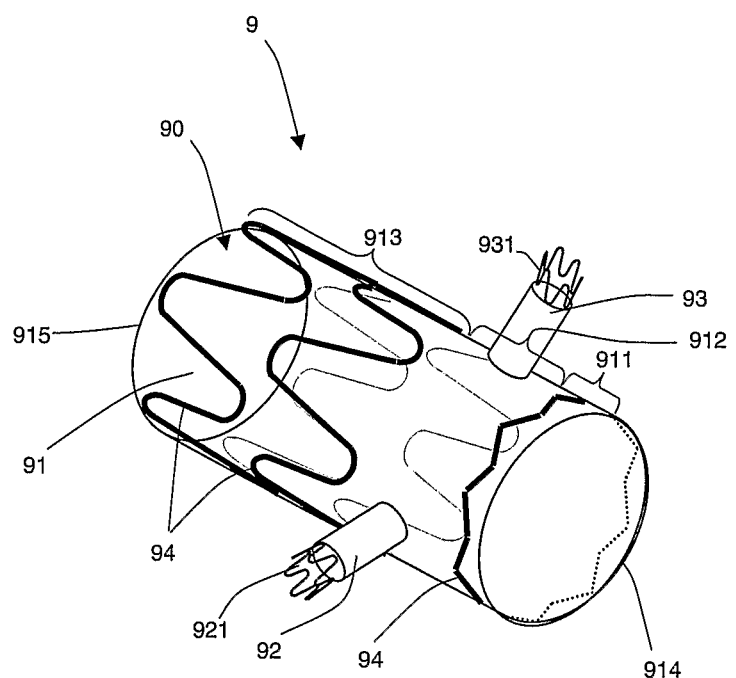
Figure 13:
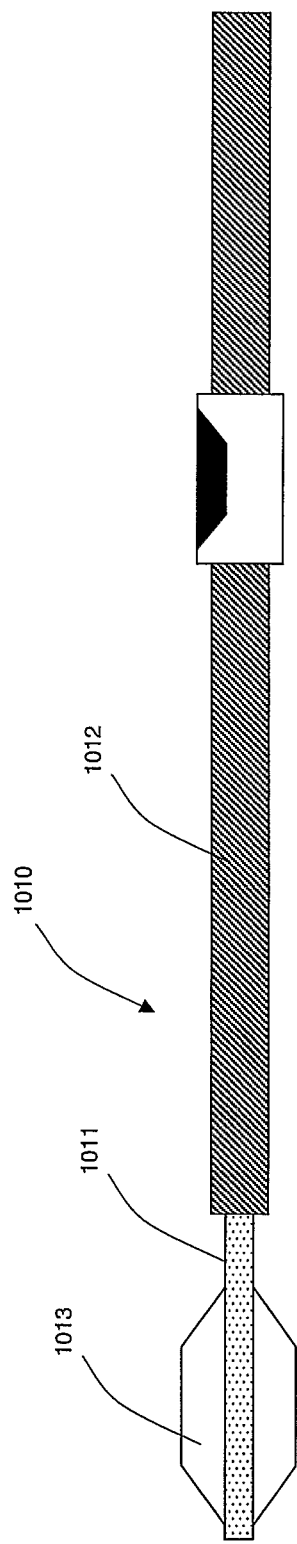
Figure 14:
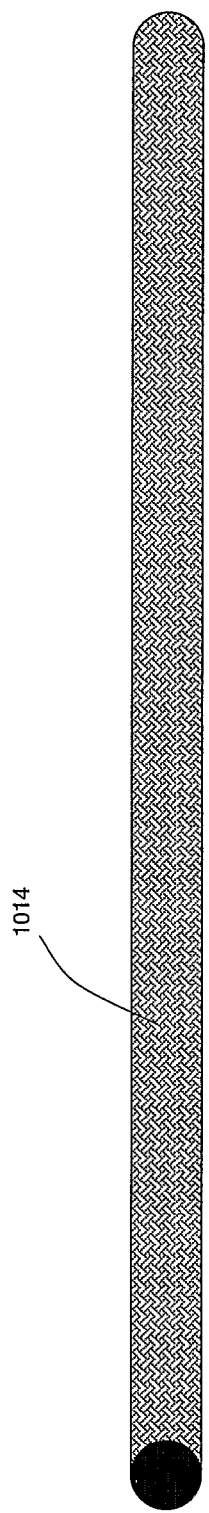
Figure 15:
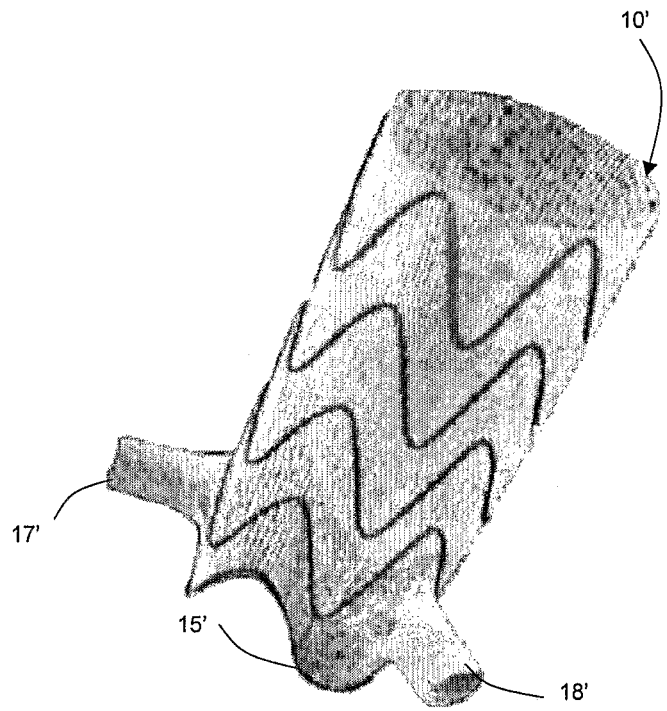
Figure 16:
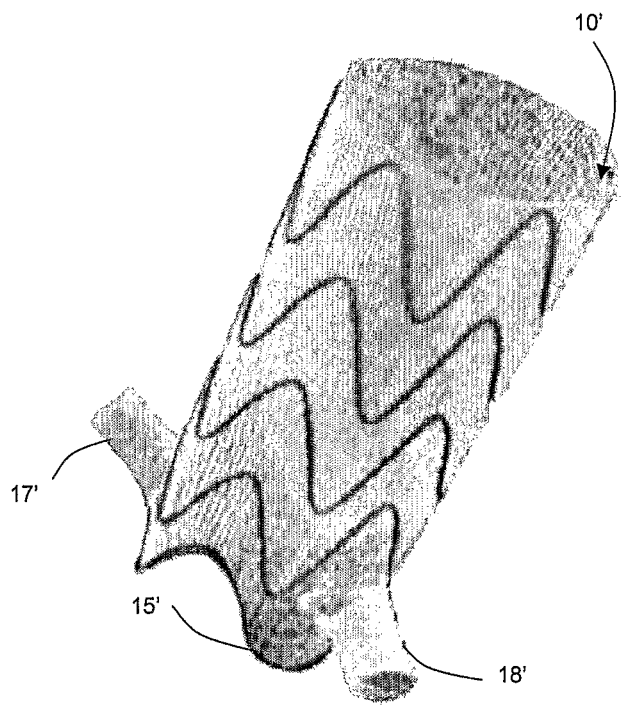
Figure 17:
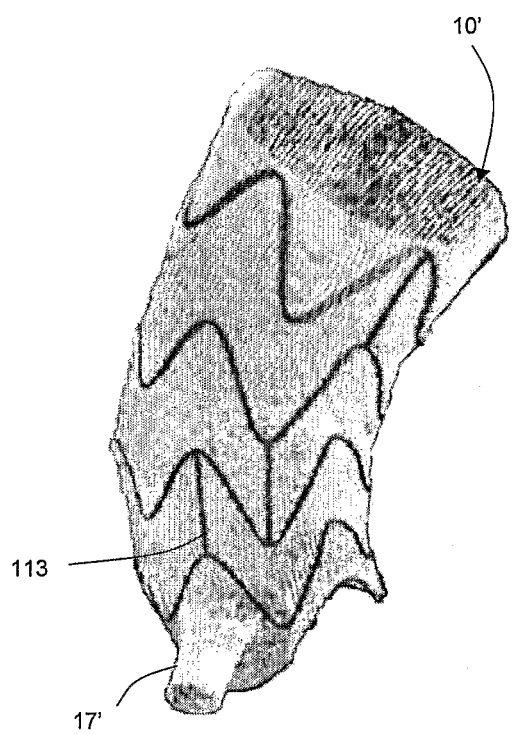
Figure 18A:
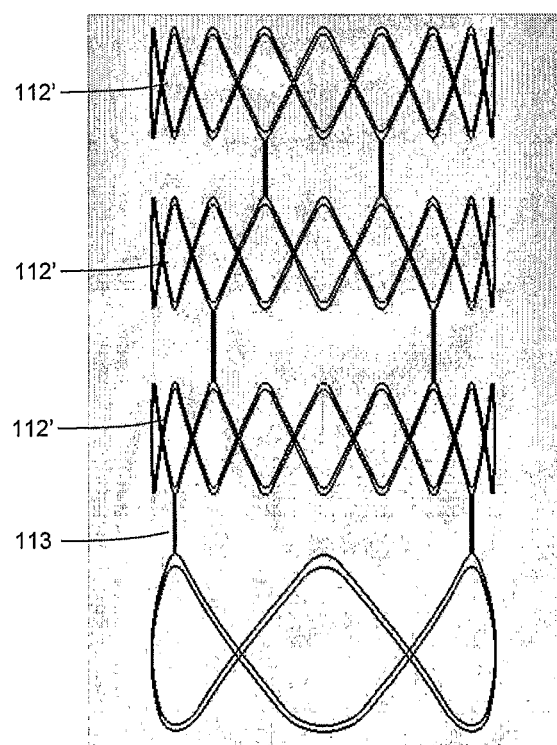
Figure 18B:
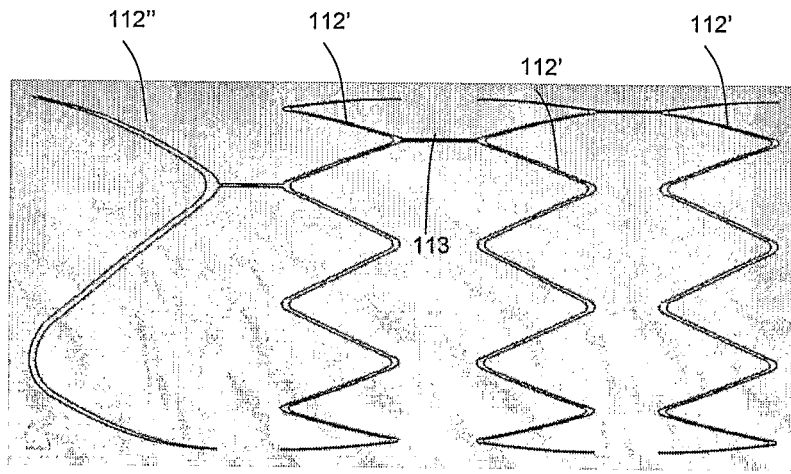
Figure 18C:
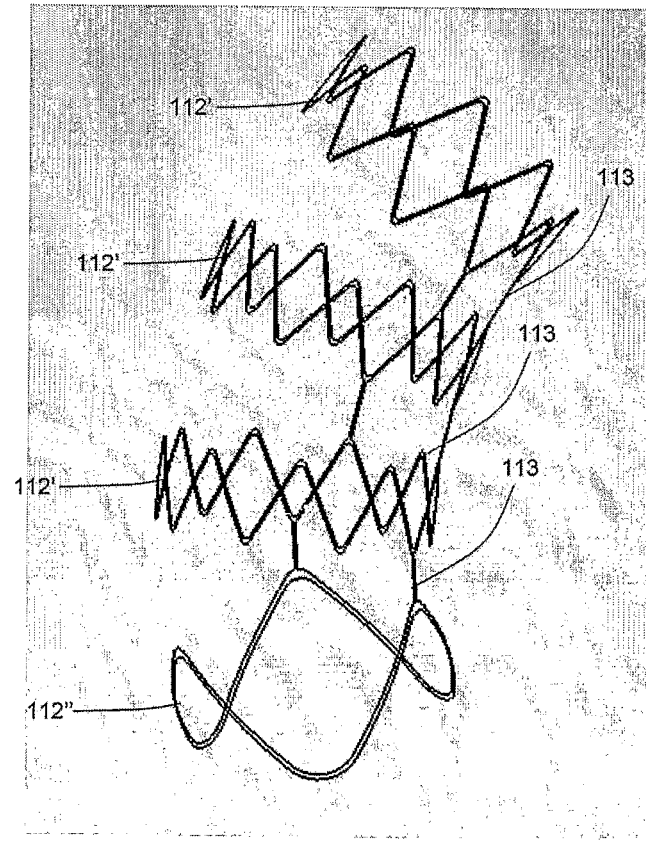
Figure 18D:
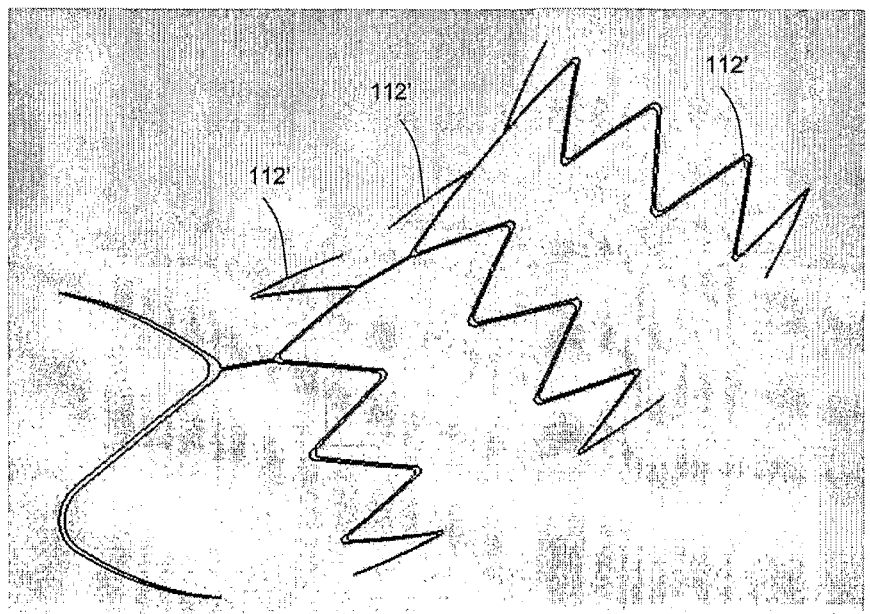
Figure 19:
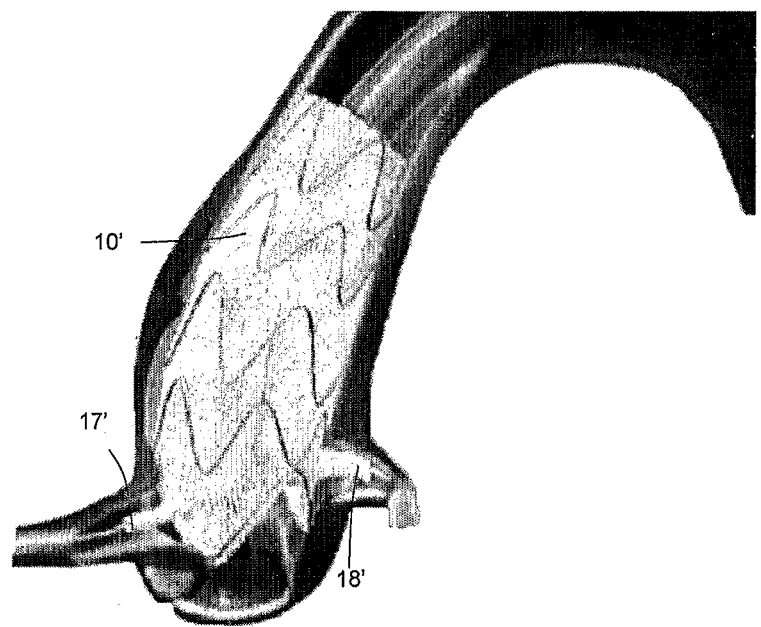

FIGS. 9a and 9b show a side view and an end view respectively of a prosthesis according to an eighth embodiment of the present invention in a contracted state, and FIGS. 9c and 9d shows side and end enlarged views of the projecting portions of the prosthesis of FIGS. 9a and 9b;

FIG. 10 shows an oblique view of a prosthesis according to a ninth embodiment of the present invention;

FIGS. 11 to 14 show side views of apparatus for delivering a prosthesis to a branch region of a blood vessel, according to an embodiment of the present invention;

FIG. 15 shows an image of a prosthesis in accordance with an embodiment of the present invention in a straight configuration;

FIG. 16 shows an image of the prosthesis of FIG. 15 with the branch conduits flexed to a degree relative to the main conduit of the prosthesis;

FIG. 17 shows an image of the prosthesis of FIG. 15 in a curved configuration;

FIGS. 18a and 18b show, respectively, front view and a simplified side view of the stent scaffold structure for the prosthesis of FIG. 15;

FIGS. 18c and 18d illustrate the manner in which the stent scaffolding enables the prosthesis to curve; and FIG. 19 illustrates the prosthesis of FIG. 15 in situ in the aortic root during deployment.

Figure 2:
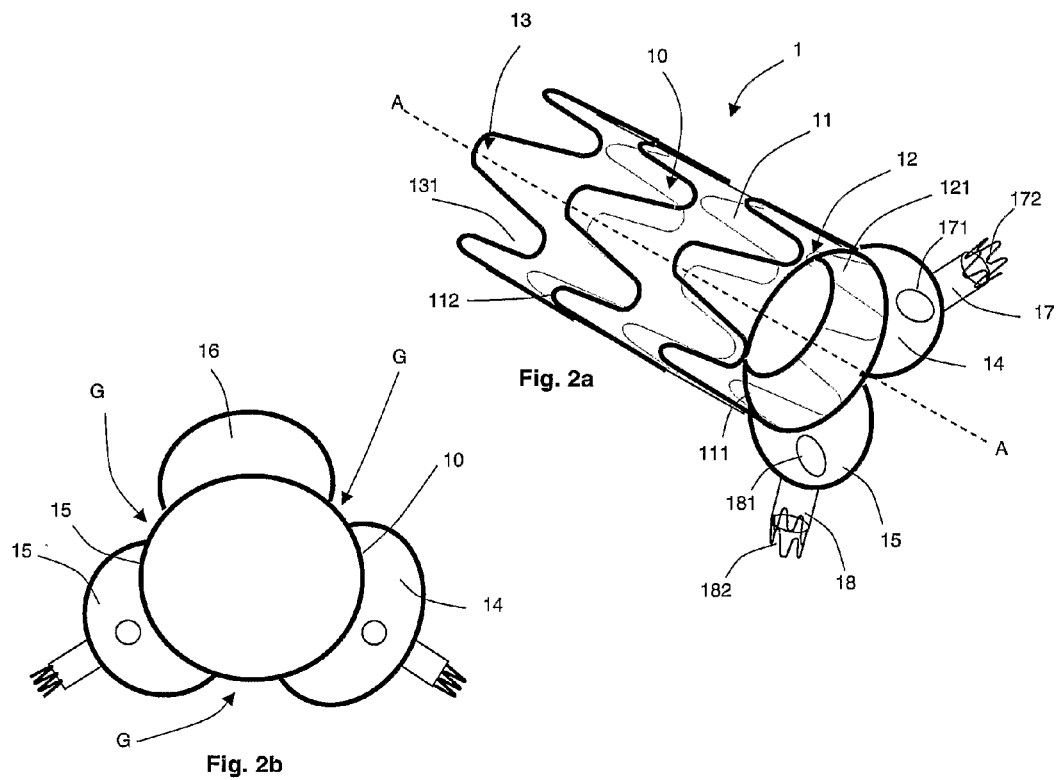
FIGS. 2a and 2b show an oblique view and an end view respectively of a prosthesis according to a first embodiment of the present invention.

With reference to FIGS. 2a and 2b, a prosthesis 1 according to a first aspect of the present invention comprises a main conduit 10 having a tubular wall portion 11 with first and second ends 12, 13, the tubular portion 11 extending between the first and second ends in the elongation direction of the tubular portion 11, which direction is indicated by line A-A in FIG. 2a. First and second openings 121, 131 are provided at the first and second ends 12, 13 of the tubular wall portion respectively. The main conduit further comprises first, second and third projecting portions 14, 15, 16 which are connected to the first end 12 of the tubular wall portion 11. The third projecting portion 16 is not shown in FIG. 2a, but is shown in FIG. 2b.

The main conduit 10 is moveable between a contracted state and an expanded state. The main conduit 10 is shown in an expanded state only in FIGS. 2a and 2b. The prosthesis may be placed in a contracted position during delivery to the branch region, so that it is less likely to be obstructed during delivery. Then, once positioned at the branch region, it may be expanded for use.

The wall material of the tubular portion 11 may be silicone coated nylon textile, which material is supported by a plurality of integral z-stents 112. The z-stents 112 may be sewn into the material, for example.

The tubular portion 11 has a substantially circular rim 111 surrounding the first opening 121. The first second and third projecting portions 14, 15, 16 are connected to the rim 111. Each projecting portion is connected to just under one third of the rim 111 in this embodiment.

The projecting portions 14, 15, 16 in this embodiment are thin-walled lobe-shaped elements. The prosthesis 1 comprises first and second branch conduits 17, 18, which are connected to the first and second projecting portions 14, 15 respectively. The branch conduits 17, 18 comprise tubular walls, which are supported by an expandable stent 172, 182, which can be expanded to anchor the branch conduits in respective branch blood vessels in use. The branch conduits 17, 18 locate over respective openings 171, 181 in the first and second projecting portions 14, 15 to permit fluid flow through the openings 171, 181 and into the branch conduits 14, 15.

Figure 1:
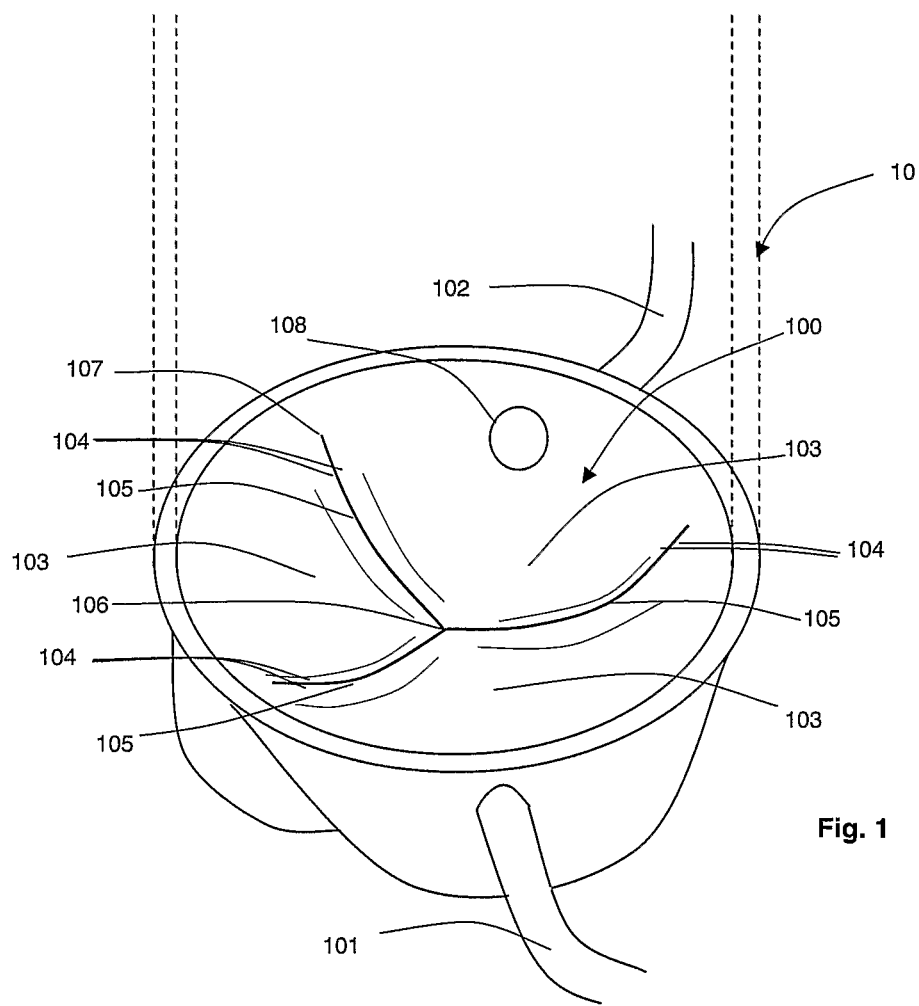
FIG. 1 shows an exemplary arrangement of the aortic root.

The prosthesis 1 is arranged to be located at the branch region of the aortic root, where the aorta meets the right and left coronary arteries. When the prosthesis 1 is deployed, the main conduit 10 is configured to be located in the ascending aorta, and the first and second branch conduits 14, 15 are configured to be located in the right and left coronary arteries respectively. By locating the first and second branch conduits 14, 15 on the projecting portions 14, 15, 16 the prosthesis 1 can extend to a position that is far enough down the ascending aorta for insertion into the coronary arteries, without interfering with aortic valve located at the aortic root, which could cause malfunction and/or damage of the valve. Specifically, the projecting portions 14, 15, 16 are arranged to extend into the bowl-shaped cavities provided by the half-moon shaped leaflets of the aortic valve (see FIG. 1), and the gaps between the projecting portions are arranged to accommodate the ridges and commissures situated between the leaflets, with little or no contact between the prosthesis 1 and the aortic valve. The gaps provided between the projecting portions are indicated generally by arrows G in FIG. 2b.

The projecting portions 14, 15, 16 project at an angle of between 30-45 degrees from the elongation direction A-A of the main conduit. This permits the projecting portions to follow more closely the contours of the aortic valve.

Figure 3:
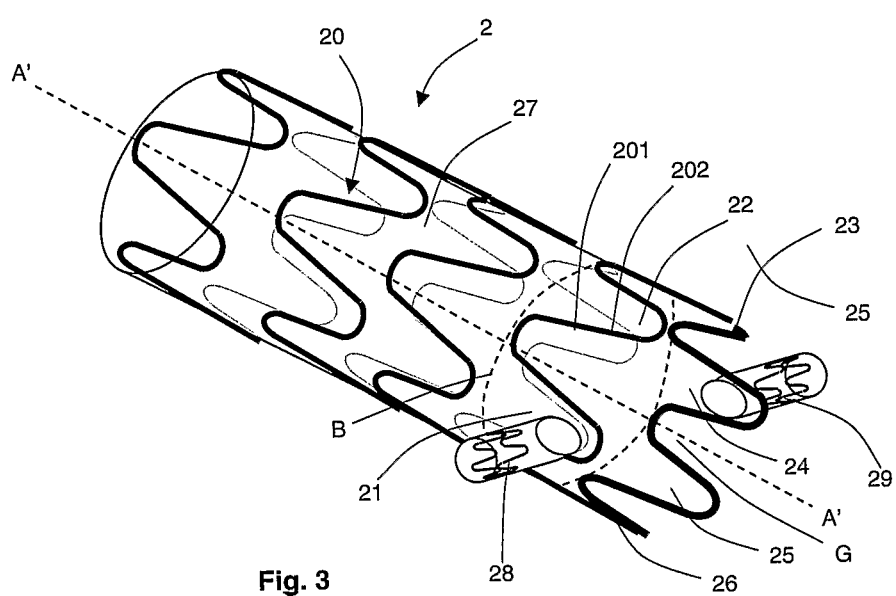
FIG. 3 shows an oblique view of a prosthesis according to a second embodiment of the present invention.

A prosthesis 2 according to a second embodiment of the present invention is shown in FIG. 3. The prosthesis 2 is similar to the prosthesis 1 described above with respect to the first embodiment of the invention, except for the arrangement of the projecting portions.

In the second embodiment, projecting portions 21-26 are provided by cut-outs in the main conduit 20, so that a lip 201 of the main conduit 20, adjacent the first end of the tubular portion 27, follows a zigzagging path of a z-stent 202 supporting walls of the main conduit 20. It can be considered that the 'zigs' of the path provide the projecting portions 21-26 of the prosthesis, and the 'zags' of the path provide the gaps G between the projecting portions, or vice-versa. In this embodiment, the zigzagging path provides the prosthesis with six projecting portions 21-26, the branch conduits 28, 29 being connected to, and extending from, two opposing projecting portions 21, 24. The first end of the tubular portion 27 is indicated by dotted line B, with the projecting portions 21-26 projecting therefrom. Nevertheless, the walls of the projecting portions 21-26 and the tubular portion 27 are one-piece. In this embodiment, the projecting portions 21-26 project in the same direction as the elongation direction of the tubular portion 27, as indicated by dotted line A'-A'.

The prosthesis 2 according to the second embodiment is intended for use in the same manner as described above with respect to the first embodiment. Although the projecting portions 21-26 are not angled relative to the elongation direction of the main conduit as the projecting portions 14, 15, 16 of the first embodiment, the projecting portions 21-26 may still follow substantially the contours of the aortic valve, and the prosthesis 2 may be simpler to manufacture than prosthesis 1 of the first embodiment of the present invention.

Figures 4A, 4B:
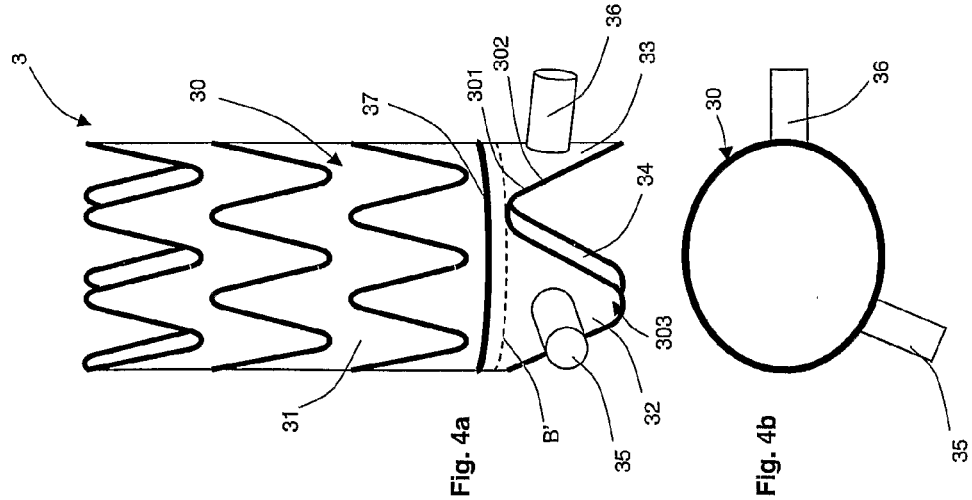
FIGS. 4a and 4b show a side view and an end view respectively of a prosthesis according to a third embodiment of the present invention.

A prosthesis 3 according to a third embodiment of the present invention is shown in FIGS. 4a and 4b. The prosthesis 3 is similar to the prosthesis 2 described above with respect to the second embodiment of the invention. However, the zigzagging path of the lip 301 and z-stent 302 provided at the first end 303 of the main conduit 30 has a lower frequency, providing the prosthesis 3 with only three, rather than six, projecting portions 32, 33, 34, the projecting portions projecting from the first end (indicated by dotted line B') of the tubular portion 31. By having only three projecting portions, 32, 33, 34, the projecting portions conform more closely to the arrangement of the three leaflets of the aortic valve, and may therefore provide a better fit. Two branch conduits 35, 36 are connected to, and extend from, two of the projecting portions 32, 33. The main conduit has a constant uniform diameter, as can be seen in FIGS. 4a and 4b.

In this embodiment, the prosthesis 3 is provided with a circumferential sealing element 37 which is intended to reduce or prevent fluid flow past the prosthesis, between the walls of the main conduit 30 and the walls of the aorta.

Figures 5A, 5B:
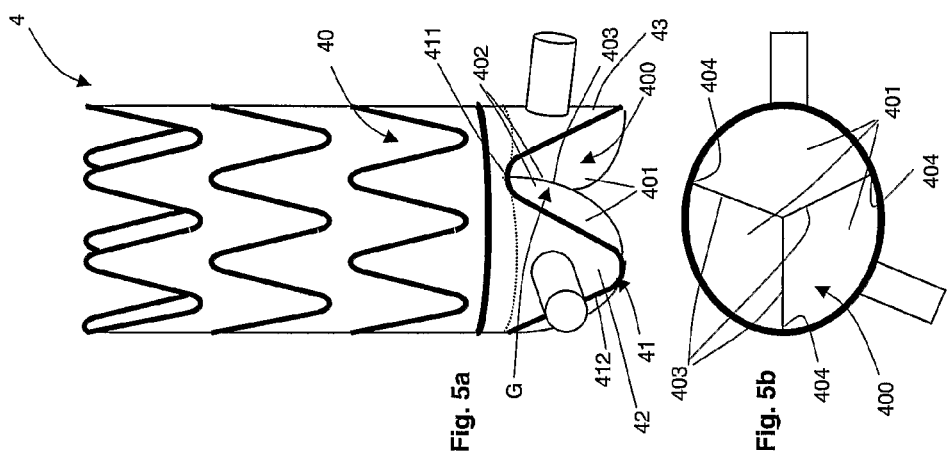
FIGS. 5a and 5b show a side view and an end view respectively of a prosthesis according to a fourth embodiment of the present invention.

A prosthesis 4 according to a fourth embodiment of the present invention is shown in FIGS. 5a and 5b. The prosthesis 4 is similar to the prosthesis 3 of the third embodiment (FIGS. 4a and 4b), except that it comprises an artificial (prosthetic) valve 400, intended to replace, or provide back up for, a damaged aortic valve.

The artificial valve 400 is located at the first end 41 of the main conduit 40 and is configured similarly to an actual aortic valve. In this regard, the artificial valve comprises three leaflets 401, side edges 402 of each leaflet 401 being releasably engaged to adjacent side edges of the other valve leaflets 401. The valve leaflets 401 are generally half-mooned shaped. The upper surfaces of the valve leaflets 401, rise up towards the side edges 402 so as to form three radially extending ridges 403. The ridges rise from a central region of the valve, to commissural points 404 of the side edges 402 (i.e. points at which the side edges are fixed together), at the periphery of the valve 400. The commissural points 404 are connected to the first end of the tubular portion proximate the inner apices 411 of the zigzagging lip 412, as seen in FIG. 5a, so that the ridges 403 of the artificial valve 400 line up with the gaps G provided between the projecting portions 42, 43.

Figures 6A, 6B:
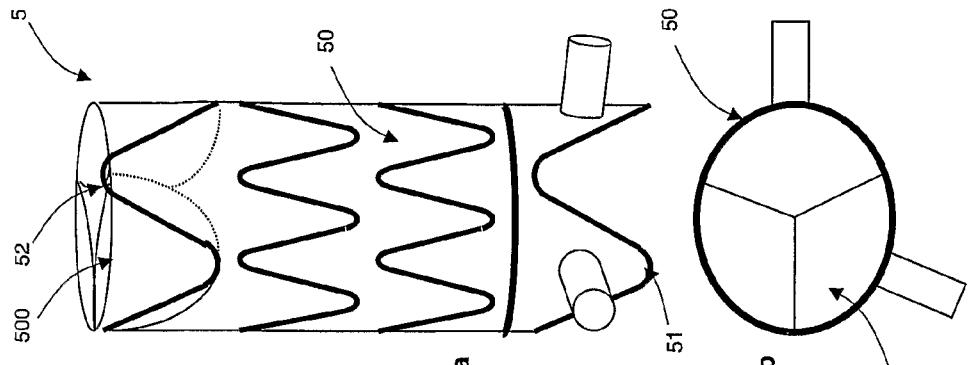
FIGS. 6a and 6b show a side view and an end view respectively of a prosthesis according to a fifth embodiment of the present invention.

A prosthesis 5 according to a fifth embodiment of the present invention is shown in FIGS. 6a and 6b. The prosthesis 5 is similar to the prosthesis of the fourth embodiment of the present invention, except that the valve 500 is provided at the second end 52 of the main conduit 50, rather than the first end 51. This ensures that there can be no interference between the artificial valve and the aortic valve 500, in use.

Although not shown, the prosthetic valve could be alternatively located at any position between the two ends of the main conduit of the prosthesis.

A prosthesis 6 according to a sixth embodiment of the present invention is shown in FIGS. 7a and 7b. The prosthesis 6 is the same as the prosthesis 3 of the third embodiment of the invention (FIGS. 4a and 4b), except for the wall material of the projecting portions 61, 62, 63 of the main conduit 60, and of the branch conduits 64, 65. In particular, walls of the first and second projecting portions 61, 62, 63 comprise an annular region 611, 621 to which the respective branch conduits 64, 65 are attached, which annular regions 611, 621 are of wall material that is more elastic and flexible than the wall material of the rest of the projecting portions 61, 62, 63 and the tubular portion 66. The branch conduits 64, 65 comprise the same wall material as the annular regions 611, 621, in this embodiment.

By arranging the branch conduits 64, 65 to connect to a more flexible and elastic region of the walls of the main conduit 60, the branch conduits 64, 65 may be moved significantly relative to each other and to the rest of the prosthesis. This provides the prosthesis 6 with greater adaptability for use at the branch region at the aortic root, which can have different anatomic configurations; the positions of the coronary ostia may vary between patients, for example. By having branch conduits 64, 65 that can move relative to each other, and the rest of the prosthesis 6, identical prostheses 6 may be used for patients even if they have coronary ostia in different positions, for example.

Figure 8:
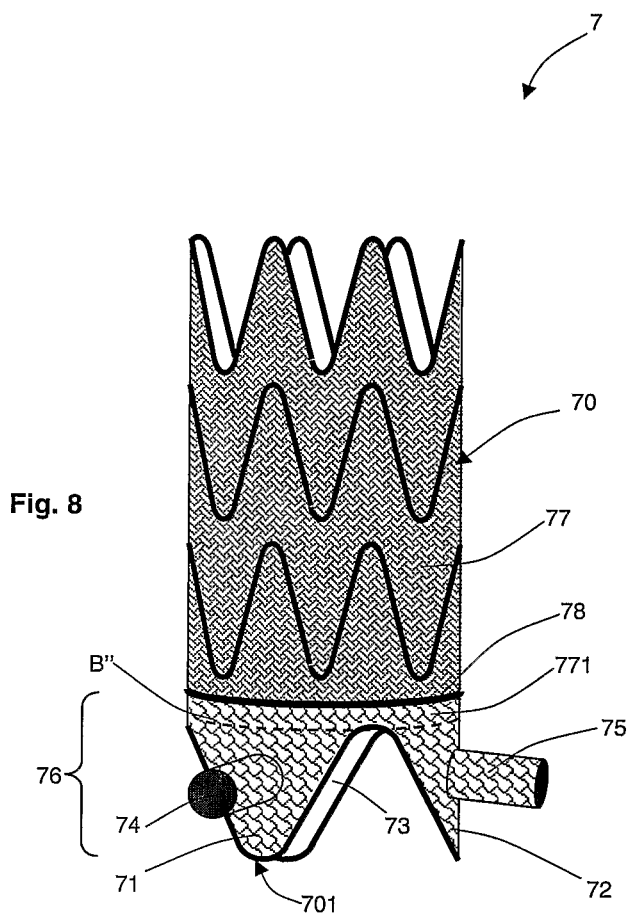
FIG. 8 shows a side view of a prosthesis according to a seventh embodiment of the present invention.

A prosthesis 7 according to a seventh embodiment of the present invention is shown in FIG. 8. The prosthesis 7 is the same as the prosthesis 6 of the sixth embodiment of the invention (FIGS. 7a and 7b), except that, rather than having annular wall regions that are flexible and/or elastic, a larger wall region, indicated by reference 76, adjacent the first end 701 of the main conduit 70, is more flexible than the rest of the main conduit 70. In particular, the wall material of the projecting portions 71, 72, 73, branch conduits 74, 75, and an annular region 771 of the tubular portion 77, between the seal 78 and the first end (indicated by dotted line B") of the tubular portion 77, is more flexible than remaining part of the tubular portion 77. Differences in the wall material are represented by the different patterns in FIG. 8. The difference in the flexibility may be achieved by providing woven wall materials with different weave profiles, for example.

A prosthesis 8 according to an eighth embodiment of the present invention is shown in FIGS. 9a to 9d. The configuration of the prosthesis is substantially the same as the prostheses of the third, sixth and seventh embodiments, except that the wall material of the projecting portions 81, 82, 83 is of sufficient flexibility that, when the main conduit 80 is placed in a contracted state as shown in the FIGS. 9a to 9d, the wall material of the projecting portions 81, 82 envelops the branch conduits 84, 85. Essentially, the branch conduits are folded into a pleat of the projecting portions 81, 82, 83 when the main conduit 80 is placed in a contracted state. The branch conduits 84, 85, folded into the projecting portions 81, 82, 83, are represented using dotted lines in FIG. 9c.

A prosthesis 9 according to a ninth embodiment of the present invention is shown in FIG. 10. The prosthesis 9 comprises a main conduit 90, having a tubular portion 91, and two branch conduits 92, 93. However, in this embodiment, no projecting portions are provided. The branch conduits 92, 93 are connected to the tubular portion 91 instead. The walls of the tubular portion 91 are supported by a scaffold of z-stents 94. In particular, a first circumferential wall section 911 at a first end 914 of the tubular portion is supported by an integral z-stent, a third circumferential wall section 913 at the second end 915 of the tubular portion is supported by two integral z-stents 94, and a second circumferential wall section 912, located between the first and third circumferential wall sections 911, 913, is substantially unsupported; it has no integral z-stents. The branch conduits 93, 94 are connected to the second circumferential wall section 912. The walls of the branch conduits 92, 93 also comprise integral z-stents 921, 931

The arrangement is such that the second circumferential wall section 912 has greater flexibility than the first and third circumferential wall sections 911, 913, because movement of this section is not restricted by supporting z-stents. Accordingly, the branch conduits 92, 93, connected to the second circumferential wall section 912, can move substantially relative to the first and third circumferential sections 911, 913, and/or each other, allowing the branch conduits 92, 93 to be positioned in branch blood vessels having different relative positions.

Although not shown, the prosthesis 9 may comprise a prosthetic valve and projecting portions, e.g. lobes, projecting from the first end 914 of the tubular portion. The lobes may extend far enough from the end of the tubular portion such that, if the prosthesis is used at the branch region of the aortic valve, and the first and second branch conduits are located in the right and left coronary arteries, the lobes will push against the leaflets of the aortic valve, and extend across the aortic valve, causing the leaflets to move apart, maintaining the aortic valve in an open position. This avoids complications that could arise from the prosthetic valve and the aortic valve functioning at the same time. The projecting portions may also help 'seat' the prosthesis appropriately.

A delivery apparatus 1000 for delivering the prosthesis according to any one of the previous embodiments is shown in FIGS. 11 to 14.

The delivery apparatus 1000 comprises an assembly 1001 for delivering the prosthesis to a blood vessel branch region, and a thin-walled PTFE inner sleeve 1002, arranged to locate over the prosthesis (not shown), and the assembly 1001, during delivery to the branch region. The inner sleeve 1002 places the main conduit of the prosthesis in a contracted stated for delivery.

The assembly 1001 comprises a central pushing core 1003, preferably of polymer material, which extends from its proximal end 1004 to its distal end 1005 in a forward direction of the apparatus. A push element 1006, which is generally cuboid in this embodiment, is connected to the distal end 1005 of the pushing core 1003 in order to engage and push the prosthesis toward the branch region. The push element 1006 has a distal end surface 1007 for abutting the main conduit of the prosthesis. The distal end surface 1007 lies along a plane which is substantially perpendicular to the elongation direction of the pushing core 1003.

The push element 1006 is wider than the central pushing core 1004. It has side (lateral) regions 1008 which extend beyond the central pushing core 1003 in a direction perpendicular to the elongation direction of the pushing core 1003. In this embodiment, two bores 1009 are provided in the side regions of the push element 1006, through which two actuators 1010 are slidably mounted. The arrangement is such that the actuators 1010, e.g. push rods, can be slid through the bores 1009 in a forward direction of the apparatus to project from the distal end of the push element 1006. The actuators 1010 each comprise a balloon catheter 1011 (see FIG. 13), which is held within a sleeve 1012. The actuators 1010 can be pushed forward from the push element 1006, to engage the branch conduits of the prosthesis and push them toward the branch blood vessels, e.g. the coronary arteries, in order to locate them within the branch blood vessels. Then, balloons 1013 of the balloon catheters 1010 can expand the branch conduits, so that they fit tightly within the coronary arteries.

The apparatus further comprises a reinforced outer liner sleeve 1014 (see FIG. 14), which is arranged to surround the inner sleeve, push assembly and prosthesis, during delivery to the branch region. In this embodiment, the sleeve is reinforced with braided material. By providing a reinforced outer sleeve such as this, the sleeve may be flexible, whilst resilient against kinking, which is particularly advantageous when the branch region is at the aortic root, and the delivery apparatus must navigate the tight bend of the aortic arch. Once the delivery apparatus reaches the branch region, the outer sleeve can be removed. Thereafter, the main conduit of the prosthesis can be expanded by retracting the inner sleeve, whereupon the main conduit can engage the sidewalls of the aorta, at the aortic root. Subsequently, the actuators can be used to push the branch conduits into the branch regions of the blood vessels, as described above.

FIGS. 15 to 19 illustrate a prosthesis in accordance with a further embodiment of the invention, similar to the prosthesis 3 of the third embodiment (FIGS. 4*a* and 4*b*). FIGS. 15 to 17 show images of the prostheses captured from a 3-D computer model and FIG. 19, also captured from the computer model, shows the prosthesis in situ in the aortic root.

The main conduit 10' can be clearly seen in these images, as well as one of three projecting portions 15' at the lower end of the main conduit 10'. Also seen are the two branch conduits 17', 18' that are connected to, and extend from, two of the projecting portions 15'.

FIG. 16 show how the branch conduits 17', 18' can be articulated relative to the side wall of the main conduit by virtue of the flexibility of the portion of the main conduit to which they are attached. As best seen in FIG. 19, this allows them to conform to the geometry of the coronary arteries within which they are deployed.

As illustrated in FIGS. 18 and 19, the main conduit 10' itself is also able to assume a curved configuration. The main conduit 10' is constrained to curve in a specific direction and to a specific extent by virtue of the construction of the stent scaffolding that supports it. The basic form of this scaffolding is illustrated in FIGS. 18*a* to 18*d*. In this example, four stents 112', 112" (e.g. Z-stents) provide circumferential support for the wall of the prosthesis. The zig-zag form of the lowermost stent 112" is wider than that of the other stents 112' and creates the basic form of the projections 15'.

The stents 112', 112" are connected to one another, spaced longitudinally along the prosthesis, by tie bars 113. These tie bars are to one side of the prosthesis (e.g. the right-hand side as seen in FIG. 18*c*). As seen in the figures, this configuration of the tie bars 113 allows the prosthesis towards the side that has the tie bars 113, as the stents 112', 112" are free to spread apart from one another on the side of the prosthesis opposite the side with the tie bars 113. By appropriate selection of the positions on the tie bars 113 the extent and direction of the possible curvature of the prosthesis can be dictated. In this example, as best seen in FIG. 18*a*, there are two tie bars 113 between each adjacent stent 112', 112". The tie bars are spaced increasingly further apart from top to bottom.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A prosthesis for locating at a branch region of an aortic root, where an aorta meets right and left coronary arteries adjacent an aortic valve having intact native leaflets, the prosthesis comprising:
    a main conduit having a tubular portion with first and second ends, and a first projecting portion projecting from the first end of the tubular portion, wherein there are no more than three portions projecting from the first end, including the first projecting portion, and
    a first branch conduit, wherein the first branch conduit is connected to, and extends from, the first projecting portion;
    wherein the main conduit and the first branch conduit are arranged for locating in the aorta and a coronary artery respectively, the first projecting portion projecting into a bowl-shaped cavity of one of three valve leaflets of the aortic valve having intact native leaflets,
    wherein the main conduit has a constant uniform diameter.

2. A prosthesis for locating at a branch region of an aortic root, where an aorta meets right and left coronary arteries adjacent an aortic valve having intact native leaflets, the prosthesis comprising:

a main conduit having a tubular portion with first and second ends, and a first projecting portion projecting from the first end of the tubular portion, wherein there are no more than three portions projecting from the first end, including the first projecting portion, and a first branch conduit, wherein the first branch conduit is connected to, and extends from:

the first projecting portion; or the tubular portion at a position adjacent the first projecting portion, wherein the main conduit and the first branch conduit are arranged for locating in the aorta and a coronary artery respectively, the first projecting portion projecting into a bowl-shaped cavity of one of three valve leaflets of the aortic valve having intact native leaflets, wherein the main conduit comprises one or more z-stents for supporting walls of the main conduit, and wherein one of the one or more z-stents is provided adjacent the first end of the tubular portion and defines outer edges of each of the no more than three projecting portions.

3. The prosthesis according to claim 2, comprising a second projecting portion projecting from the first end of the tubular portion, wherein the no more than three projecting portions includes the second projecting portion, and a second branch conduit connected to, and extending from:

the second projecting portion; or the tubular portion at a position adjacent the second projecting portion;

wherein the second branch conduit is arranged for locating in a second coronary artery, the second projecting portion projecting into a bowl-shaped cavity of a second one of the three leaflets of the aortic valve having intact native leaflets.

4. The prosthesis according to claim 2, wherein the first branch conduit is connected to, and extends from, the first projecting portion.

5. The prosthesis according to claim 2, wherein each of the no more than three projecting portions is a lobe.

6. The prosthesis according to claim 2, wherein each of the no more than three projecting portions extend in the same direction as an elongation direction of the tubular portion.

7. The prosthesis according to claim 2, comprising a circumferential sealing element on an outer side of the tubular portion.

8. The prosthesis according to claim 2, wherein the prosthesis can be moved between a contracted and an expanded state.

9. The prosthesis according to claim 8, wherein the prosthesis is arranged such that, when the prosthesis is placed in the contracted state, walls of the no more than three projecting portions that have any branch conduit connected or adjacent to them envelop the branch conduits.

* * * * *